United States Patent

Pennig

[11] Patent Number: 5,433,719
[45] Date of Patent: Jul. 18, 1995

[54] FIXATION PIN FOR SMALL-BONE FRAGMENTS

[76] Inventor: Dietmar Pennig, Hans-Driesch-Strasse 12, 50935, Koln, Germany

[21] Appl. No.: 214,365

[22] Filed: Mar. 16, 1994

[30] Foreign Application Priority Data

Mar. 25, 1993 [DE] Germany ............. 43 09 707.3

[51] Int. Cl.⁶ ............................................. A61B 17/56
[52] U.S. Cl. .................................. 606/73; 411/401; 411/424; 411/368
[58] Field of Search ............ 606/72, 73, 69, 65; 411/401, 411, , 424, 368, 155, 156, 544, 542, 426; 24/486, 453

[56] References Cited

U.S. PATENT DOCUMENTS

| | | | |
|---|---|---|---|
| 1,105,105 | 7/1914 | Sherman | 606/73 X |
| 3,037,221 | 6/1962 | Lanius, Jr. | 411/155 X |
| 4,059,102 | 11/1977 | Devas | 606/73 |
| 4,524,765 | 6/1985 | Zbikowski | 606/73 X |
| 4,662,365 | 5/1987 | Gotzen | |
| 5,176,016 | 3/1993 | Buser et al. | 606/73 X |

FOREIGN PATENT DOCUMENTS 0424734  5/1991  European Pat. Off. .

OTHER PUBLICATIONS

Ships in Scale, p. 2, Sep./Oct. 1983 Planking Screw Advertisment & Photocopy.

*Primary Examiner*—Peter A. Aschenbrenner

[57] ABSTRACT

The invention contemplates a fixation pin for retaining small bone fragments in an osteosynthesis procedure. The pin comprises a smooth-walled shank portion and an adjoining threaded portion, wherein a step-down conical shoulder is formed between the shank portion and the threaded portion.

10 Claims, 1 Drawing Sheet

FIXATION PIN FOR SMALL-BONE FRAGMENTS

BACKGROUND OF THE INVENTION

The present invention relates to a fixation pin for use in retaining small-bone fragments in an osteosynthesis procedure.

It is generally known in osteosynthesis to fix bone fragments by screws or pins. In the case of small-bone splinterings, the screws or pins available in the prior art are, however, much too large to fix a small splintered portion of a given bone to another portion of the same bone without damaging these parts. The fixing of such small bone fragments by means of simple pins or nails is therefore problematical, since there is no abutment to hold the parts together, and the bone may shift on the outer wall of the pin or nail.

BRIEF STATEMENT OF THE INVENTION

The object of the present invention is to provide a fixation pin for bone fragments which, despite its necessarily small size, will produce a dependable fixation of small-bone fragments.

The invention achieves this object by providing a small-bone pin with an elongate smooth-walled shank, the distal end portion of the pin having step-down transition to a smaller-diameter threaded portion. The step-down transition is effectively a conical shoulder which can abut a bone splinter while the threaded portion is anchored to the main part of the same bone.

Stated in other words, a small-bone pin of the invention has a smooth-walled shank portion along a relatively large part of the overall length of the pin, and a relatively short threaded part adjoining the lower end of said shank portion. In use of this pin, the threaded portion is screwed into the bone fragment and the remaining or main fraction of the same small bone; the upper side of the bone fragment is abutted by the conical step formed between the threaded portion and the shank portion, so that it is no longer possible for the bone fragment to slide on the pin.

When relying solely upon the small-bone pin of the invention the shank portion may be located within surrounding muscular tissue. The shank portion also projects externally, for easy cut-off to desired length, using a suitable tool; in that event, it would seem appropriate to refer to the bone pin of the invention as a compression wire.

Optionally, and depending upon the shape of the proximal face of the bone fragment to be secured, a special washer is applicable over the threaded portion of the pin (a) with a counterbore adapted to locate on the conical step, (b) with a larger diameter than that of the shank portion of the pin, and (c) with a concave distal face adapted for relatively large-area retaining engagement with the bone fragment.

DETAILED DESCRIPTION

The preferred embodiment will be described in conjunction with the accompanying drawings, in which.

Figure 1:
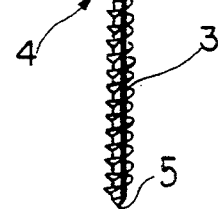
FIG. 1 is an enlarged view in elevation of a small-bone pin of the invention.
Figure 2:
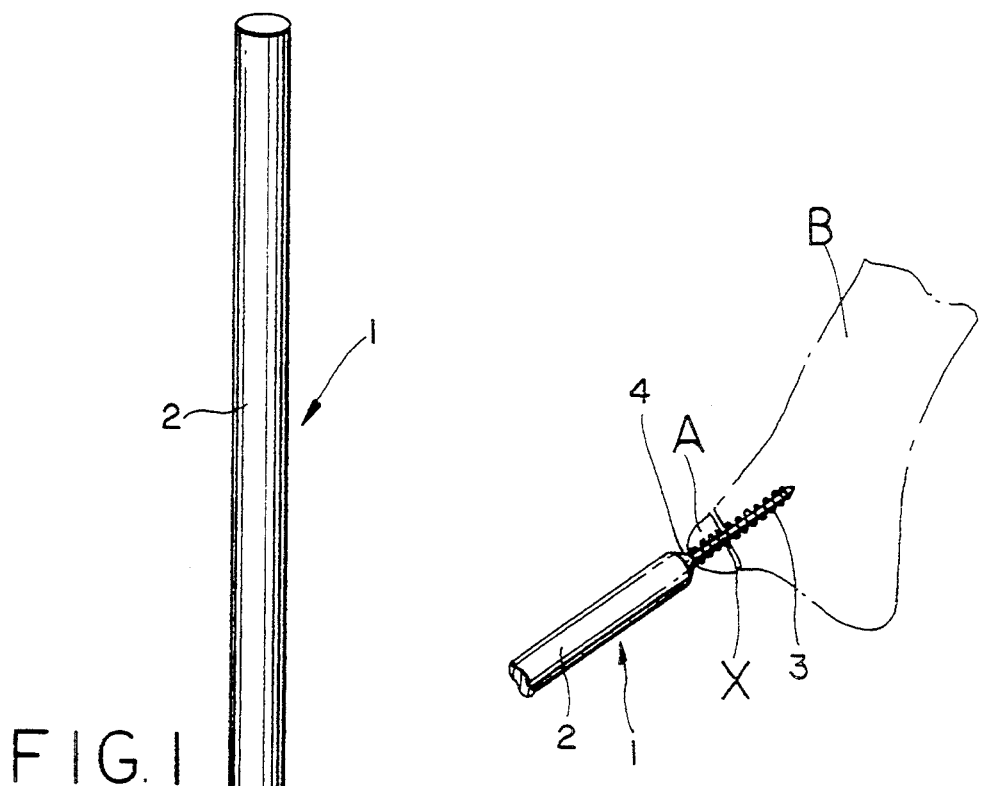
FIG. 2 is a simplified section, on a reduced scale, through a small bone, fractured at X, to show use of the invention.

In FIG. 1, a small-bone fixation pin or compression wire 1 is seen to comprise essentially a smooth-walled shank portion 2, with an adjoining distal threaded portion 3. The outside diameter of the threaded portion 3 is smaller than the outside diameter of the shank portion 2; the diameter of the threaded portion is preferably constant, except for a sharp distal end 5, for self-tapping entry into bone tissue. Between the threaded portion 3 and the shank portion 2, as seen in FIG. 2, a frusto-conical shoulder or step 2 serves as an abutment for a bone fragment A which is to be fixed onto the remainder of the main bone B, by advancing the threaded portion 3 into the main bone.

The half-angle of conical convergence, i.e., with respect to the central axis of pin 1, is suitably in the range 30° to 60°, and is preferably about 45°.

To obtain an idea of the sizes involved, it is pointed out that a fixation pin 1 can, for example, have a length of 100-mm, with the threaded portion 3 having a length of 15-mm and the shank portion 2 a length of 85-mm. The diameter of the threaded portion can be 1.4 to 1.6-mm when, for example, the diameter of the shank portion 2 is 2-mm. Stated in other words, the diameter of the threaded portion is in the range of approximately 70 to 80 percent of the diameter of the shank portion.

With the indicated orders of magnitude, the shank portion 2 can easily be cut off by suitable nippers so that protruding regions of the threaded portion or of the shank portion can easily be removed.

Figure 3:
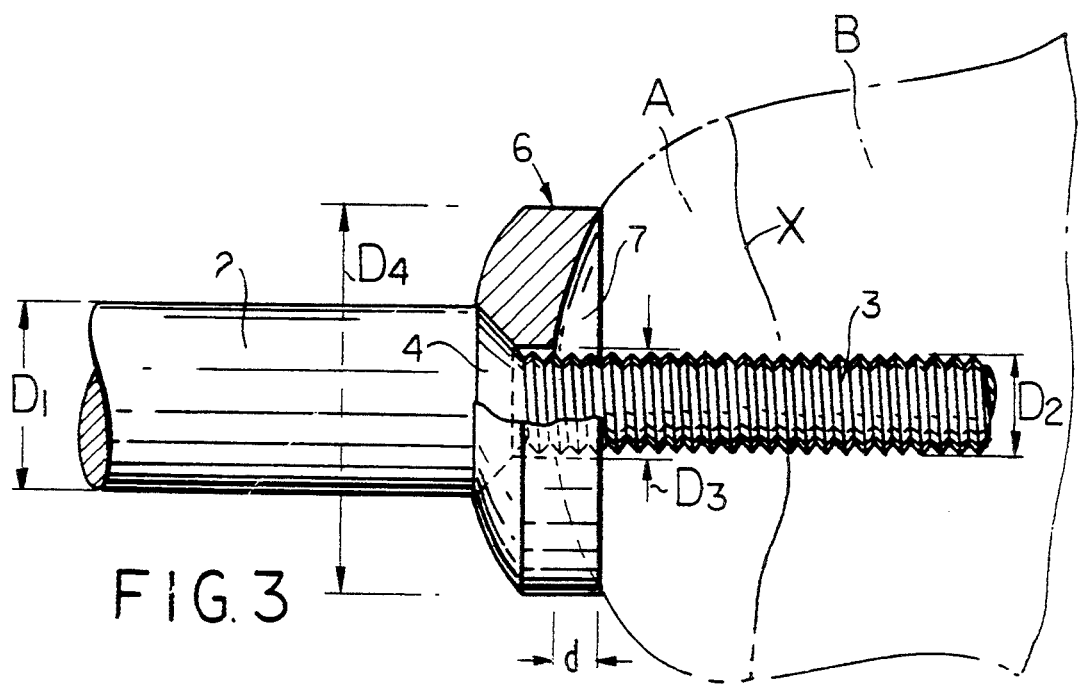
FIG. 3 is a greatly enlarged fragmentary view of coacting elements of the invention in an installed condition, pursuant to an optional employment of kit components of the invention.

Depending upon the externally exposed shape of a particular bone fragment to be secured to the remainder of the same bone, the invention is shown in FIG. 3 to permit optional employment of a washer 6, which, as in the case of pin 1, is also preferably and suitably of stainless steel. In FIG. 3, diametric dimensions $D_1$ and $D_2$ identify the sizes and size relationships discussed above for the shank and threaded portions (2, 3) of the pin 1.

Washer 6 features a bore of diameter $D_3$ to clear the threads of portion 3 and a conical counterbore in its proximal face, adapted for centering engagement with the frusto-conical step 4. Washer 6 has an outer diameter $D_4$ in the range 1.5 to 2.5 times the shank diameter $D_1$, and its distal face 7 is concave, being suitably a circular or parabolic arc of revolution about the axis of the bone pin. The axial depth d of the concavity 7 may suitably be about one third of the axial extent of washer 6; the bore diameter $D_3$ may be approximately another third of the axial extent, and the remaining axial extent is the depth of the conical counterbore.

In FIG. 3, the small bone fragment B is of course greatly enlarged but is seen to present a convex shape for washer (6) engagement, with the convex bone shape in close conformance with the concave depth and curvature of the distal face 7 of the washer. This is as it should be for the fracture X as shown in FIG. 3, wherein bone-engagement via distal face 7 provides an enlarged area of bone-fragment support and compression surrounding the region of threaded-portion (2) engagement to bone at A and at B.

It is realized, however, that not all bone fragments will present a convex shape that is so well accommodated by the distal face 7 that has been described. To best equip the orthopedic surgeon who must deal with whatever confronts him, the invention is to be understood as being available in kit form, wherein at least one and preferably several washers 6 are provided for each bone screw, pin, or wire 1, and wherein the several washers 6 differ as to axial depth d of the concavity 7. The surgeon has further opportunity to adapt the described washer 6 to particular circumstances of small bone fragment contour, in that the washer 6 may be bent as necessary by pliers or other tools which are standard equipment for the orthopedic surgeon. Thus, if need be, a washer 6, of preselected axial depth d of its otherwise spherical distal face 7 may be bent to distort the distal face 7 into a more complex curvature wherein the curvature is, for example, (i) of relatively short-focus parabolic nature in a first longitudinal section which includes the pin axis and (ii) of longer-focus parabolic nature in a second longitudinal section, taken 90 degrees from the first longitudinal plane.

A kit of the nature indicated preferably includes a set of small-bone pins or compression wires 1, wherein there is at least one pin or wire 1 of each of several shank (2) diameters, illustratively of 3-mm, 2-mm, and-/or 1.6-mm diameter, with thread (3) diameters of 2.2-mm, 1.6-mm, and/or 1.2-mm, respectively. Such a kit would include a set of washers 6 at least to fit the 3-mm and 2-mm shank sizes indicated, and with at least two different axial depths d for each of these shank sizes. In the case of the 3-mm shank size, washers 6 are suitably of 6-mm diameter $D_4$; and in the case of the 2-mm shank size, washers 6 are suitably of 4-mm diameter $D_4$.

What is claimed is:

1. In combination, a fixation pin for fastening a small broken bone fragment (A) to a main remaining part (B) of the same bone, said fixation pin comprising a smooth-walled shank portion of diameter substantially 3 mm or less, said pin having a threaded portion of reduced diameter connected to said shank portion via a transitional formation, said threaded portion having a sharp distal end that is self-tapping in bone tissue, and a washer having a bore sized for free reception of said threaded portion and for seating at said transitional formation, said washer having an outer diameter greater than the diameter of said shank portion, and said washer having a distal face for relatively large-area contact with a bone fragment (A) when the distal end of said threaded portion is otherwise fully engaged to said main bone part (B) via said bone fragment (A).

2. A kit comprising a fixation pin for fastening a small broken bone fragment (A) to a main remaining part (B) of the same bone, said fixation pin comprising a smooth-walled shank portion of diameter substantially 3 mm or less, said pin having a threaded portion of reduced diameter connected to said shank portion via a transitional formation, said threaded portion having a sharp distal end that is self-tapping in bone tissue, and a washer having a bore sized for free reception of said threaded portion and for seating at said transitional formation, said washer having an outer diameter greater than the diameter of said shank portion, said washer having a distal face for relatively large-area contact with a bone fragment (A) when the distal end of said threaded portion is otherwise fully engaged to a main bone part (B) via a small broken fragment (A) of the same bone.

3. A kit as in claim 2, wherein the outer diameter of said washer is at least twice the outer diameter of said shank portion.

4. The combination of claim 1, in which said pin is made from a material such that the shank portion may be cut to required length by a suitable nipper tool.

5. A fixation pin according to claim 4, in which said material is stainless steel.

6. In combination, a fixation pin for fastening a small broken bone fragment (A) to a main remaining part (B) of the same bone, said fixation pin comprising a smooth-walled shank portion (2) and a threaded portion of reduced diameter connected to said shank portion (2) via a frusto-conical transitional formation having a half angle of conical convergence of at least 30 degrees, and a washer having a bore sized for free reception of said threaded portion, said washer having an outer diameter greater than the diameter of said shank portion, said washer having a proximal face with a convergent counterbore in substantial conformance with said frusto-conical transitional formation, said washer having a distal face that is a dished concavity for relatively large-area contact with a convex profile of a bone fragment (A).

7. A kit comprising a fixation pin for fastening a small broken bone fragment (A) to a main remaining part (B) of the same bone, said fixation pin comprising a smooth-walled shank portion (2) and a threaded portion of reduced diameter connected to said shank portion (2) via a frusto-conical transitional formation having a half angle of conical convergence of at least 30 degrees, a washer having a bore sized for free reception of said threaded portion, said washer having an outer diameter greater than the diameter of said shank portion, said washer having a proximal face with a convergent counterbore in substantial conformance with said frusto-conical transitional formation, said washer having a distal face that is a dished concavity for relatively large-area contact with a convex profile of a bone fragment (A).

8. A kit as in claim 7, wherein said washer is one of a plurality of washers of different outer diameter.

9. A kit as in claim 7, wherein said washer is one of a plurality of washers having dished concave distal end faces of different axial depth.

10. A kit as in claim 7, wherein the outer diameter of said washer is at least twice the outer diameter of said shank portion.

* * * * *